(12) United States Patent
Ramirez-Arizmendi et al.

(10) Patent No.: US 7,420,170 B2
(45) Date of Patent: Sep. 2, 2008

(54) FOURIER TRANSFORM INFRARED (FTIR) CHEMOMETRIC METHOD TO DETERMINE CETANE NUMBER OF DIESEL FUELS CONTAINING FATTY ACID ALKYL ESTER ADDITIVES

(75) Inventors: Luis Ramirez-Arizmendi, South Riding, VA (US); Heather D. Hamje, Green Lane, PA (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/651,184

(22) Filed: Jan. 9, 2007

(65) Prior Publication Data
US 2007/0163168 A1 Jul. 19, 2007

Related U.S. Application Data

(60) Provisional application No. 60/759,410, filed on Jan. 17, 2006.

(51) Int. Cl.
*G01N 21/35* (2006.01)

(52) U.S. Cl. .............................. 250/339.08
(58) Field of Classification Search ............ 250/339.08
See application file for complete search history.

(56) References Cited

U.S. PATENT DOCUMENTS

| | | | |
|---|---|---|---|
| 5,121,337 A | 6/1992 | Brown | |
| 5,578,090 A | 11/1996 | Bradin | |
| 6,223,133 B1 | 4/2001 | Brown | |
| 6,707,043 B2 * | 3/2004 | Coates et al. | 250/339.09 |

* cited by examiner

*Primary Examiner*—David P. Porta
*Assistant Examiner*—Marcus H Taningco
(74) *Attorney, Agent, or Firm*—Paul E. Purwin

(57) ABSTRACT

The present invention is a method to determine the cetane number of a diesel fuel containing a fatty acid alkyl ester including determining the infrared spectrum of the fuel and correlating the spectrum to the cetane number using a multivariate-based Mid-FTIR model. The fatty acid alkyl ester may be rapeseed methyl ester and the infrared spectrum includes the frequency ranges 4900-3500 $cm^{-1}$ and 2200-1624 $cm^{-1}$ or the frequency ranges 4900-3500 $cm^{-1}$ 2200-1800 $cm^{-1}$ and 1700-1624 $cm^{-1}$.

10 Claims, 2 Drawing Sheets

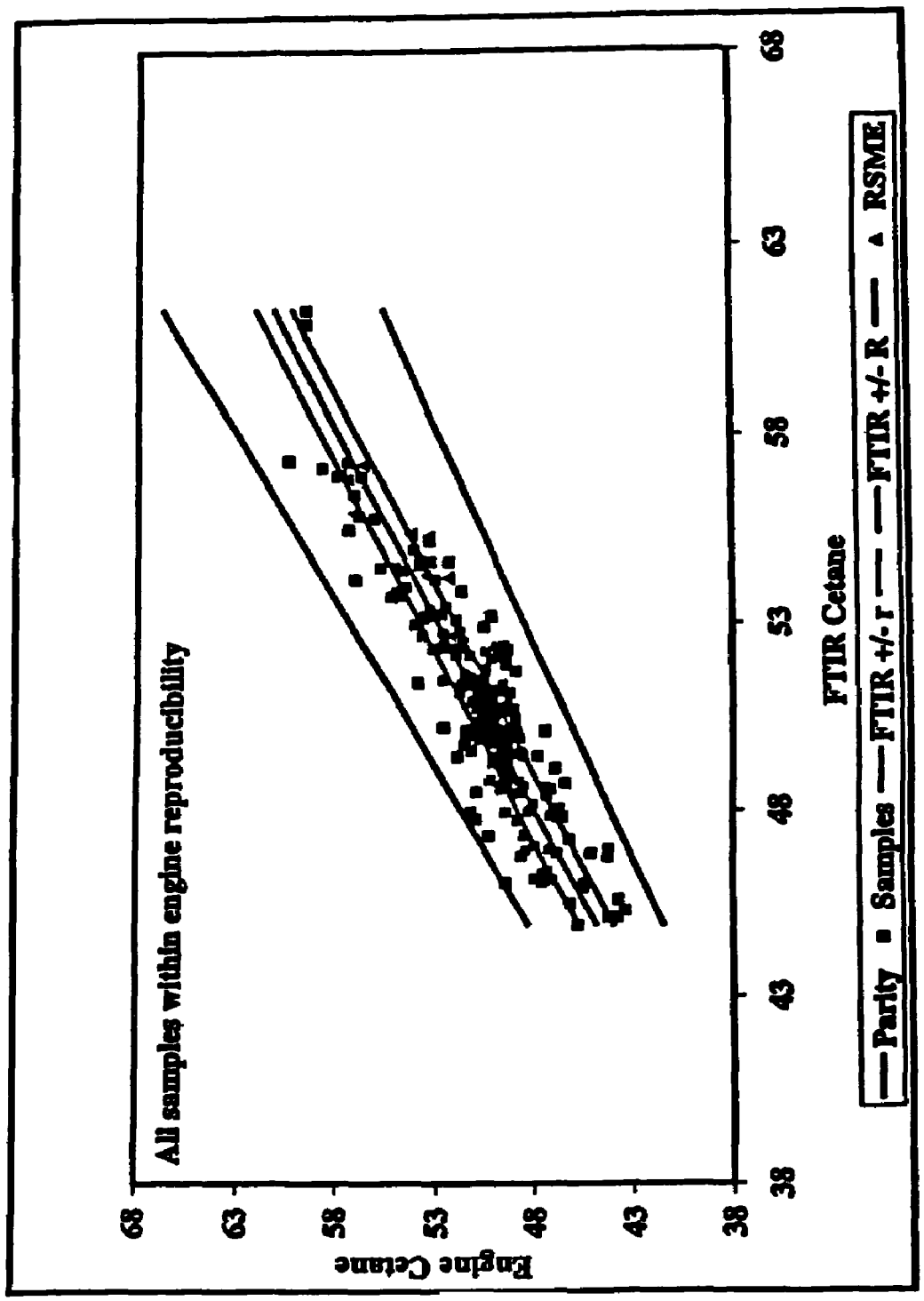
Figure 1. Calibration Parity Plot - FTIR Cetane Number Model B

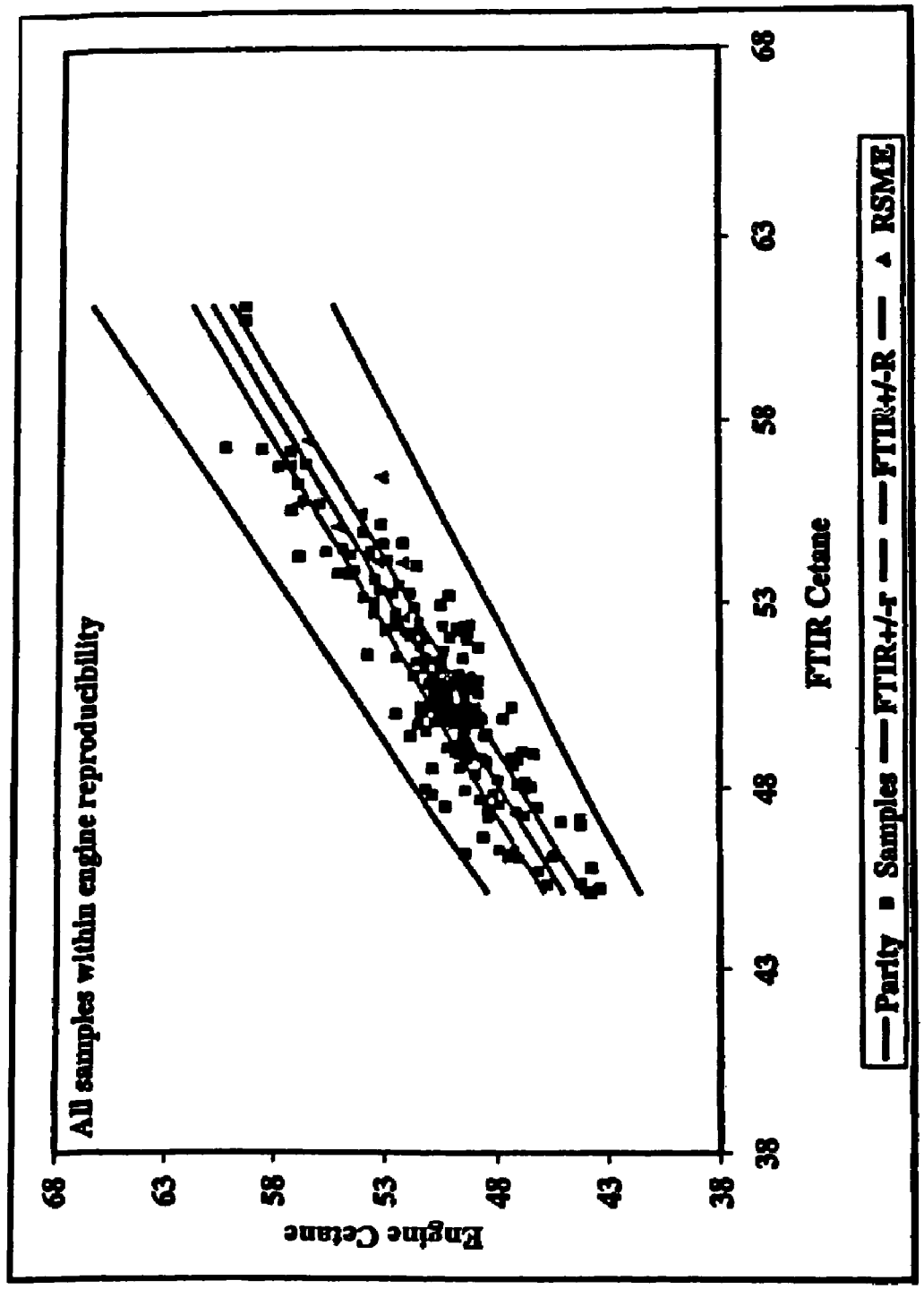
Figure 2. Calibration Parity Plot - FTIR Cetane Number Model C

FOURIER TRANSFORM INFRARED (FTIR) CHEMOMETRIC METHOD TO DETERMINE CETANE NUMBER OF DIESEL FUELS CONTAINING FATTY ACID ALKYL ESTER ADDITIVES

CROSS-REFERENCE TO RELATED APPLICATION

This application claims the benefit of U.S. Provisional application 60/759,410 filed Jan. 17, 2006.

BACKGROUND OF THE INVENTION

The present invention is a method to determine the cetane number of diesel fuels containing a fatty acid alkyl ester using multivariate fourier transform infrared models. In particular, the method determines the cetane number of diesel fuels containing rapeseed methyl ester.

The European Union is encouraging the use of rapeseed methyl ester (RSME) as a blending component of diesel fuel at levels up to 5% (from hereon known as biodiesel). The cetane number of such diesel fuels is measured in the laboratory by using an engine test method (ASTM D613). This method is not capable of measuring cetane number online, it is time consuming and requires a highly trained operator. As a result, a faster, repeatable method is needed to measure cetane number of biodiesel that could be used for process control and/or to certify the quality of products real-time, as they are being produced (i.e., online certification). Fourier Transform Infrared (FTIR) chemometric modeling can be employed to estimate the cetane number of diesel fuels online or in a laboratory. However, current FTIR methods involve chemometric models incapable of recognizing RSME-containing fuels, and, thus cannot be used for control of biodiesel production or certification.

Currently, an engine is used to measure cetane number of diesel fuels. The operation of the engine is carried out in a laboratory by a skilled operator. The engine analysis is time consuming, uses up a lot of fuel and it is not very repeatable (r=0.9 cetane number). An FTIR analyzer can be used as an alternative method to provide a direct measurement of cetane number online or in the laboratory. The FTIR analysis is fast and repeatable. However, the determination of cetane number of diesel fuels containing RSME by using chemometric data from Mid-FTIR spectroscopic analyzers has not been demonstrated. As a result, a method is needed to expand the use of FTIR spectroscopy to measure cetane number of diesel fuels with blended RSME.

SUMMARY OF THE INVENTION

The present invention is a method to determine the cetane number of diesel fuels containing a fatty acid alkyl ester additive (i.e., rapeseed methyl ester (RSME)). The method involves the utilization of an FTIR-based multivariate/chemometric model in a preferred embodiment to correlate a measured infrared spectrum of a biodiesel sample to its cetane number. The two regions of the infrared spectrum employed in the determination of the cetane number include the frequency ranges 4900-3500 $cm^{-1}$ and 2200-1624 $cm^{-1}$. In another preferred embodiment, the infrared spectrum used in the analysis includes three frequency ranges: 4900-3500 $cm^{-1}$, 2200-1800 $cm^{-1}$ and 1700-1624 $cm^{-1}$. Three regions are used in the analysis only when the absorption band associated with the ester functional group (~1746 $cm^{-1}$) exceeds the linear range of the infrared detector (i.e., at ~1.5 absorbance units).

BRIEF DESCRIPTION OF THE DRAWINGS

FIG. 1 shows a calibration parity plot for the model of Example 1.

FIG. 2 shows a calibration parity plot for the model of Example 2.

DETAILED DESCRIPTION OF THE PREFERRED EMBODIMENTS

The use of rapeseed methyl ester (RSME) as a diesel fuel blending component to reduce exhaust emission by diesel engines is increasing. Current Mid FTIR-based chemometric models cannot be used in quality or process control of RSME-containing fuels (i.e., biodiesel) because the models do not recognize these fuels. The present invention can be employed to determine the cetane number of fuels encompassing rapeseed methyl ester. The invention involves the use of two or three infrared regions in the development of the FTIR-based multivariate model. The number of regions used depend on whether or not the frequency of the characteristic ester functional group of the blend component (~1746 cm-1) is included in the model. A total of 23 diesel samples doped with RSME (0.5, 1.0, 1.5, 2.0, 2.5, 3.0, and 5 vol %) were added into a calibration set used to develop several FTIR cetane number models. The models utilize known chemometric software to correct for baseline variations and water vapor interferences (see U.S. Pat. No. 5,121,337). The resulting FTIR models are now capable of recognizing RSME-containing fuels, and thus, able to determine cetane number of diesel fuels containing this component. These methods to FTIR model development for subsequent diesel fuel analysis can be used in process control applications and/or release of RSME-containing diesel products.

An FTIR-based model (Model A) was developed earlier to be used for cetane number prediction of diesel fuels. The model is based on data collected on base and cetane-improved fuels from several fuel refineries in Europe. However, samples containing RSME (rapeseed methyl ester), which will be increasingly used as a blending component in European diesel over the next few years, were not included in the calibration set used to build the model. As a result, RSME-containing fuels are not recognized by the model.

Experiments were carried out to develop an FTIR-based method that could be used for measuring cetane number of RSME-containing fuels. The method involves two chemometric approaches that depend on whether two or three mid-infrared (MIR) spectral regions are used for model development.

Results and Discussion

A total of 23 samples containing various concentrations of RSME (0.5, 1.0, 1.5, 2.0, 2.5, 3.0, 5.0 vol %) were prepared. After collection of FTIR spectra of these fuels, they were added to a diesel fuel dataset, which was then divided into a calibration and pre-validation set by using a genetic algorithm.

Model Development

The samples used as a training set for the development of FTIR models total 241 (14 containing RSME), with 1205 engine measurements.

EXAMPLE 1

Two Spectral Regions

Two regions from the IR spectrum were used to develop the FTIR linear Model B. The frequency ranges included are, 1) 4900-3500 cm$^{-1}$, and 2) 2200-1624 cm$^{-1}$. The latter spectral range includes the frequency of the characteristic ester functional group of RSME (~1746 cm$^{-1}$). The calibration results are shown in the parity plot in FIG. 1. As can be seen in FIG. 1, all cetane predictions by FTIR fall within the Reproducibility (R) of the engine. The Standard Error of Calibration (SEC), used as a measure of the difference between cetane values estimated by the model and the values measured by the engine for the samples in the calibration set, was calculated to be 1.5 (Table 1). This value compares well with that of Model A (SEC=1.5). Most importantly, Model B recognizes all of the RSME-containing samples, and, contrary to Model A, samples representing an extrapolation of the model (i.e., spectral outliers) were not detected in the calibration set.

TABLE 1

Calibration for Cetane Number Model B

| # Samples | # Observations | Property | SEC |
| --- | --- | --- | --- |
| 241 | 1205 | Cetane Number | 1.5 |

EXAMPLE 2

Three Spectral Regions

A different approach was used to develop Model C. The method consists of excluding the spectral region of the ester group of RSME (~1746 cm$^{-1}$) when constructing the model. The frequency ranges used are: 1) 4900-3500 cm$^{-1}$, 2) 2200-1800 cm$^{-1}$, and 3) 1700-1624 cm$^{-1}$. This approach is attractive for use in those applications for which the absorbance of the ester group of RSME exceeds the linear range of the spectrometer. As for the previous models, the SEC for Model C was calculated to be 1.5. FIG. 2 shows the calibration parity plot associated with the three spectral regions approach. None of the RSME-containing samples appear a spectral outliers.

Comparison with Current Approach

Table 2 shows cetane number predictions on randomly selected samples taken from the diesel dataset and analyzed using Model A, and the approaches described herein (i.e., two or three spectral regions). As can be seen, Model A is not capable of predicting cetane number of diesel fuels containing the RSME component accurately since these samples appear as outliers in the analysis. However, Models B and C (two and three spectral regions, respectively) clearly recognize these fuels. In addition, the cetane number predictions for samples without RSME are not affected by the use of the new approaches.

TABLE 2

Comparison of Cetane Number Predictions on Selected Samples

| Sample Coding | RSME Level (vol %) | Cetane Number (Cetane Engine) | Cetane Number (Model A) | Cetane Number (Model B; 2 Regions) | Cetane Number (Model C; 3 Regions) |
| --- | --- | --- | --- | --- | --- |
| MG1FEE01 | 0.0 | 54.9 | 53.67 | 53.73 | 53.77 |
| MG5ABBB1 | 0.0 | 51.62 | 51.46 | 51.66 | 51.84 |
| MG5BH001 | 0.0 | 52.85 | 53.21 | 53.24 | 53.24 |
| MC7N0010 | 1.0 | 53.58 | 49.96 (1) | 54.27 | 54.09 |
| MC7N0013 | 2.0 | 52.35 | 45.31 (1) | 52.66 | 52.59 |
| MC7N0014 | 3.0 | 54.77 | 43.63 (1) | 53.56 | 53.79 |
| MC7N0020 | 5.0 | 55.38 | 40.88 (1) | 53.69 | 55.06 |

(1) Model outlier due to the presence of RSME

What is claimed is:

1. A method to determine the cetane number of a diesel fuel containing a fatty acid alkyl ester comprising determining the infrared spectrum of said fuel using FTIR, determining the absorption band associated with the ester functional group and applying a chemometric model which excludes said absortion band if it exceeds the linear range of the infrared detector.

2. The method of claim 1 wherein said fatty acid alkyl ester is rapeseed methyl ester.

3. The method of claim 1 wherein said infrared spectrum includes the frequency ranges 4900-3500 cm$^{-1}$ and 2200-1624 cm$^{-1}$.

4. The method of claim 1 wherein said infrared spectrum includes the frequency ranges 4900-3500 cm$^{-1}$, 2200-1800 cm$^{-1}$ and 1700-1624 cm$^{-1}$.

5. The method of claim 1 wherein the IR spectrum includes frequencies that are characteristic of fatty alkyl esters.

6. The method of claim 1 wherein the IR spectrum includes frequencies that are characteristic of rapeseed methyl ester.

7. The method of claim 1 wherein said method is corrected for baseline variations.

8. The method of claim 1 wherein said method is corrected for water vapor interferences.

9. The method of claim 1 wherein said method is corrected for baseline variations and water vapor interferences.

10. The method of claim 1 wherein said correlation is determined by a model using data that is divided between a calibration set and pre-validation set by a genetic algorithm.

* * * * *